United States Patent
Kustov et al.

(10) Patent No.: US 6,414,197 B1
(45) Date of Patent: *Jul. 2, 2002

(54) PREPARATION OF PHENOL AND ITS DERIVATIVES

(75) Inventors: Leonid Modestovich Kustov; Viktor Ignatyevich Bogdan; Vladimir Borisovich Kazansky, all of Moscow (RU)

(73) Assignee: General Electric Company, Schenectady, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/078,253

(22) Filed: May 13, 1998

(30) Foreign Application Priority Data

Jul. 5, 1997 (RU) .......................................... 97112675

(51) Int. Cl.[7] .......................... C07C 39/02; C07C 37/00; C07C 39/10; B01J 29/06
(52) U.S. Cl. ....................... 568/700; 568/716; 568/764; 568/765; 568/771; 568/800; 502/63; 502/64; 502/71
(58) Field of Search ................................ 568/700, 716, 568/771, 764, 765, 800; 502/63, 64, 71

(56) References Cited

U.S. PATENT DOCUMENTS

| | | | |
|---|---|---|---|
| 4,367,359 A | 1/1983 | Kaeding | 585/467 |
| 4,559,314 A | 12/1985 | Shihabi | 502/85 |
| 4,581,215 A | 4/1986 | Kaeding | 502/71 |
| 4,724,270 A | 2/1988 | Chang et al. | 585/408 |
| 4,950,829 A | 8/1990 | Han et al. | 502/77 |
| 4,982,013 A | 1/1991 | Gubelmann et al. | 568/771 |
| 5,001,280 A | 3/1991 | Gubelmann et al. | 568/716 |
| 5,055,623 A | 10/1991 | Gubelmann et al. | 568/800 |
| 5,110,995 A | 5/1992 | Kharitonov etal. | 568/741 |
| 5,508,244 A * | 4/1996 | Watanabe et al. | 502/64 |
| 5,672,777 A | 9/1997 | Kharitonov et al. | 568/754 |
| 5,808,167 A | 9/1998 | McGhee | 568/716 |
| 5,849,257 A | 12/1998 | Fujiwara et al. | 423/404 |
| 5,892,132 A * | 4/1999 | Rooks et al. | 568/771 |
| 6,255,539 B1 | 7/2001 | Uriarte et al. | 568/800 |

FOREIGN PATENT DOCUMENTS

| | | |
|---|---|---|
| DE | 19634406 A | 3/1998 |
| EP | 0 068 755 A2 | 1/1983 |
| EP | 0 134 331 A1 | 3/1985 |
| EP | 0 302 636 A1 | 2/1989 |
| EP | 0 568 913 A2 | 11/1993 |
| JP | 56-77234 | 6/1981 |
| JP | 56-87527 | 7/1981 |
| JP | H9-194412 | 7/1997 |
| WO | WO 95 27560 | 10/1995 |
| WO | WO 95/27691 | 10/1995 |
| WO | WO 98/25698 | 6/1998 |

OTHER PUBLICATIONS

Uriarte, Anthony K., "Direct Hydroxylation Benzene to Phenol by Nitrous Oxide", 3rd World Congress on Oxidation Catalysis, Sep. 21–26, 1997.

Zholobenko, V., "Preparation of Phenol over Dehydroxylated HZSM–5 Zeolites", Mendeleev Commun. 1993, p. 28–29.

Iwamoto, et al., "Catalytic Oxidation by Oxide Radical Ions", J. Phys. Chem., 1983, v. 87, No. 6, p. 903.

Sobolev, V., "Catalytic Properties of ZSM–5 Zeolites in $N_2O$ Decomposition: The Role of Iron", Journal of Catalysis, 139, p. 453–43 (1993).

Kharitonov, A.S., "Ferrisilicate Analogs of ZSM–5 Zeolites as Catalysts For One–Step Oxidation of Benzene to Phenol", Applied Catalysis, 98, p. 33–43 (1993).

Panov, G.I., "Oxidative Hydroxylation Using Dinitrogen Monoxide: A Possible Route for Organic Synthesis Over Zeolites", Applied Catalysis, 98, 1–20 (1993).

Volodin, A., J., "The Role of Surface α–Oxygen in Formation of Cation Radicals at Benzene Adsorption on ZSM–5", Phys. Chem 1994, 98, 7548–7550.

(List continued on next page.)

*Primary Examiner*—Gary Geist
*Assistant Examiner*—Everett White

(57) ABSTRACT

A method and a catalyst are described for selective oxidation of aromatic compounds (e.g., benzene and its derivatives) into hydroxylated aromatic compounds (e.g., corresponding phenols). For example, benzene can be converted into phenol with a yield of at least 30–40%, and a selectivity on the basis of benzene of at least 95–97%. The selectivity for this reaction based on $N_2O$ is at least 90–95%. Therefore, no substantial $N_2O$ decomposition or consumption for complete benzene oxidation to $CO+CO_2$ or other side products occurs. Similar results are obtained with benzene derivatives (e.g., fluorobenzene, difluorobenzene, phenol), although the selectivity is somewhat lower in the case of derivatives (e.g., about 80–85% in the case of fluorosubstituted benzenes). A preferred catalyst for this process is a composition containing a high-silica pentasil-type zeolite (e.g, an HZSM-5 type zeolite) which contains no purposefully introduced additives such as transition or noble metals. The catalytic effect is achieved by performing a specific zeolite modification with strong Lewis acid-base centers of a specific nature. This modification can be achieved by a pretreatment comprising two steps: a first conventional calcination step at 300–600° C., and a second high-temperature calcination step at 600–950° C.

20 Claims, No Drawings

OTHER PUBLICATIONS

Bogdan, V.I., et al. *Selective Oxidation of Fluorobenzenes on Modified Zeolites Using N2O as an Oxidant, Catalysis by Microporous Materials, Studies in Surface Science and Catalysis,* vol. 94, pp. 635–640, 1995, H.K. Beyer, H.G. Karge, I. Kiricsi and J.B. Nagy (Editors), Elsevier Science B.V. N.D. Zelinsky Institute of Organic Chemistry, Russian Academy of Sciences, Moscow, 117334 Russia.

Bolshov, V.A., et al. *Radical Intermediates in the Photoinduced Formation of Benzene Cation–Radicals Over H–ZSM–5 Zeolites* J. Phys. Chem. 1994, 98, pp. 7551–7554, May 10, 1994, American Chemical Society 1994 Boreskov Institute of Catalysis, Siberian Branch of the Russian Academy of Sciences, Novosibirsk 630090, Russia.

Cesar, Marcos A., "One–Step Benzene (BTOP)" (literature) 1998 PEP Client Conference, Redwood Shores, CA May 4–5, 1998.

Kustov, L.M., et al., *NOx Adsorption Complexes on Zeolites Containing Metal Cations and Strong Lewis Acid Sites and Their Reactivity in CO and CH4 Oxidation: A Spectroscopic Study Zeolites: A Refined Tool for Designing Catalytic Sites* N.D. Zelinsky Institute of Organic Chemistry, Russian Academy of Sciences, Moscow, Leninsky prosp. 47, 117334 Russia pp. 409–415, L. Bonnevoit and S. Kaliaguine (editors), Elsevier Sciences B.V. 1995.

Uvarova, E.B., et al., *Catalytic Activity and Active Sites in Zeolite Catalysts for N2O Decomposition Zeolite Science 1994: Recent Progress and Discussions, Studies in Surface Science and Catalysis,* vol. 98 pp. 148–149, H.G. Karge and J. Weitkamp (editors), Elsevier Science B.V., 1995 N.D. Zelinsky Institute of Organic Chemistry, Russian Academy of Sciences, Moscow, Russia.

Zholobenko, V.L., et al., *The Role of Lewis Acid in Sites in Adsorption and Activation of Oxygen in Redox Type Reactions on Zeolites* Proceedings of the 9th International Zeolite Conference, Montreal, 1992, vol. 2, 299–307, Von Ballmoos, Ronald, Higgins, John B., Treacy, Michael M.J., (Editors), N.D. Zelinsky Institute of Organic Chemistry, Russian Academy of Sciences, Moscow, Lenisnsky prosp. 47, 117334, Russia, Butterworth–Heinemann: Boston, Mass 1993.

Zholobenko, V.L., et al., *Study of Active Centers for Oxidation of Benzene and Formation of Cation–Radicals in H–ZSM–5 and H–Mordenite* Kinetics and Catalysis, vol. 30, Nr. 4, 1989 pp. 901–905 (translation).

"One–Step Phenol Process Offers Higher Yield" Chementator, Edited by Ken Fouhy, Chemical Engineering/Feb. 1997, p. 15.

"New Catalyst Softens Condition for Bisphenol–A Production", Chementator, Edited by Ken Fouhy, Chemical Engineering/Feb. 1997, p. 15.

* cited by examiner

PREPARATION OF PHENOL AND ITS DERIVATIVES

BACKGROUND OF THE INVENTION

This application claims rights of priority under 35 U.S.C. § 119 based on Russian Patent Application No. 97112675, filed Jul. 5, 1997.

1. Field of the Invention

This invention is related to the field of organic synthesis, and in particular, to the methods for preparing hydroxylated aromatic compounds (e.g., phenol and its derivatives), by selective oxidation of aromatic compounds (e.g., benzene and its derivatives), with gaseous mixtures comprising nitrous oxide in the presence of heterogeneous catalysts. Commercial zeolites or zeolite-containing catalysts modified by special treatments described herein are used as heterogeneous catalysts.

2. Description of the Prior Art

Various processes are known in the art for preparing phenol and its derivatives, such as diphenols, cheorophenols, fluorophenols, alkylphenols and the like. Known processes include direct oxidation of aromatic hydrocarbons or their derivatives with $O_2$, $N_2O$ or other gaseous oxidants in the presence of oxide catalysts such as those referenced in U.S. Pat. No. 5,110,995. However, the majority of the known oxide catalysts for the direct oxidation of benzene to phenol in the presence of molecular oxygen, do not provide high selectivity and yield of the target product. The most successful example of such a catalyst is prepared from phosphates of various metals. In particular, $ZnPO_4$ has been used as a catalyst for benzene oxidation into phenol in the presence of alcohols.

At temperatures of 550–600° C., the $ZnPO_4$ catalyst produced a phenol yield of about 25%. However, the selectivity of $ZnPO_4$ was poor (60%) [Japan Patent No. 56-77234 and 56-87527, 1981]. Furthermore, phosphate catalysts are disadvantageous for benzene oxidation because they consume substantial quantities of alcohols.

Vanadium-, molybdenum-, or tungsten-based oxide catalyst systems for direct benzene oxidation with nitrous oxide ($N_2O$) at 500–600 ° C. are known [Iwamoto et al., J. Phys. Chem., 1983, v. 87, no. 6, p. 903]. The maximum phenol yield for such catalysts in the presence of an excess of steam is about 7–8%, with a selectivity of 70–72%. The main drawbacks of these catalysts are their low selectivity and yield of phenol, the required high temperatures for the reaction, and the requirement to add steam.

Zeolite catalysts are also available for the selective oxidation of benzene and its derivatives using $N_2O$ as an oxidant (E. Suzuki, K. Nakashiro, Y. Ono, Chem. Lett., 1988, no. 6, p. 953-1 M. Gubelmann et al., Eur. Pat., 341,165, 1989-1 M. Gubelmann et al., U.S. Pat. No. 5,001, 280, 1990). Specifically, high-silica ZSM-5 type pentasil zeolites are used as catalysts for oxidation of benzene, chlorobenzene, and fluorobenzene into corresponding phenols. The oxidation of benzene with nitrous oxide on HZSM-5 zeolite at 400° C. leads to the formation of phenol with a yield up to 16%, and a selectivity close to 98–99%. The disadvantage of these catalysts is that they have low conversion rates, low yields of phenol and low selectivity at high reaction temperatures.

The zeolites of the pentasil type (e.g., ZSM-5, ZSM-11, ZSM-12, ZSM-23), mordenite, zeolite Beta and EU-1, which are all modified with small iron additives during their synthesis, are known systems for performing this catalytic reaction. For example, in U.S. Pat. Nos. 5,672,777 and 5,110,995, experimental results are presented for benzene oxidation with nitrous oxide at 275–450° C. The contact time was 2–4 sec, the liquid space velocity of benzene was 0.4 $h^{-1}$, and the molar benzene : $N_2O$ ratio was 1:4. The phenol yield typically reached 20–30%, and the selectivity was 90–97%. The disadvantages of these catalysts include the necessity to introduce iron ions into the zeolite and to control the oxidation state of iron ions, the low liquid space velocity value of benzene, the significant contact time necessary to obtain acceptable, but not impressive yields of the final product, and the low selectivity at elevated temperatures (~450 C).

An HZSM-5 type catalyst that is dehydroxylated at a high temperature is also known in the art (V.L. Zholobenko, Mend. Commun., 1993, p. 28). This high temperature dehydroxylation pretreatment was found to increase the phenol yield from ~12 to ~20–25 wt. % at the $N_2O$:benzene ratio of 4:1. However, this catalyst also produced a low yield of phenol. In the process described above, the high-temperature dehydroxylation was performed in one stage with no control of the nature of the zeolite active sites. Therefore, in this process, the formation of both framework and extra framework active sites was quite possible. The significant disadvantage of all these methods is that they require a large excess of $N_2O$ over the hydrocarbon (e.g., benzene) to provide more complete conversion of the hydrocarbon to the desired oxidation products.

Another method of benzene oxidation was proposed in the patent by Panov G. I. et al. (PCT W095/27691). In this method, an excess of benzene over $N_2O$ was used (up to 9:1), and the selectivity of $N_2O$ conversion into phenol was improved. However, in this case, the catalyst contained iron as an active component Such catalysts are problematic because the oxidation state of the iron introduced into such a catalyst must be controlled. Also, the yield of phenol barely exceeded 20 wt. %, although the benzene liquid hourly space velocity (hereinafter "LHSV") was increased as compared to the previous systems to about 2–2.5 $h^{-1}$.

In another known method, phenol is produced by oxidative hydroxylation of benzene and its derivatives with nitrous oxide at 225–450° C. in the presence of an iron-containing zeolite catalyst. This zeolite catalyst is pretreated at 350–950° C. in steam containing 0.1–100 mol. % $H_2O$ (Kharitonov A. S., et al., U.S. Pat. No. 5,672,777, 1997— Russian Patent No. 2074164, C07C 37/60, June 1997-1 Application No. 94013071/04, C07C 37/60, 27.12.1995). However, treatment of the zeolite catalyst using this method does not cause a substantial increase in the activity. Another drawback of this method is the low stability of the resultant catalyst, which deactivates during the oxidation process due to the formation of tar-like side-products. Another disadvantage of all the methods described above is the low partial pressures of benzene in the vapor mixture—the benzene content was 5 mol. % and the partial pressure of benzene was about 40 torr.

Thus, an object of the present invention is to develop a method of preparing hydroxylated aromatic compounds (e.g., phenol and derivatives) by selective oxidation of aromatic compounds (e.g., benzene and its derivatives). Specifically, it is an object of the invention to use $N_2O$ as a mild oxidant in the presence of an appropriate catalyst that enhances productivity of the oxidation process by increasing the yield of hydroxylated aromatics and selectivity for the target product. It is a further object of the invention to simultaneously minimize the consumption of $N_2O$ by decreasing the oxidant-to-hydrocarbon ratio in the feed, and increasing the efficiency of $N_2O$ conversion to the desired oxidation products. It is also an object of the invention to avoid producing side products.

SUMMARY OF THE INVENTION

The objects of the invention are accomplished by a method of preparing hydroxylated aromatic compounds (e.g., phenol or its derivatives) by oxidation of aromatic compounds (e.g., benzene and derivatives) with nitrous oxide. The method of the present invention significantly increases the process efficiency due to the increase in the activity and selectivity of the catalyst, and the increase in the yield of the target products (i.e., hydroxylated aromatic compounds). In order to achieve these results, the aromatic compounds are oxidized using nitrous oxide at 225–500° C. in the presence of a zeolite catalyst. The zeolite catalyst according to the invention is modified with strong Lewis acid-base sites of a specific nature. These sites can be introduced into the zeolite catalyst by performing a special high-temperature pretreatment. This preliminary thermal activation of the H-form of zeolite is carried out in two steps. In the first step, the catalyst is heated at 350–450° C. for 4–6 h in an inert gas (nitrogen or helium) or air stream. In the second step, the catalyst is calcined at 450–1000° C. for 1–3 h in a continuous flow of an inert gas or air followed by cooling the zeolite catalyst to the reaction temperature (typically 300–450° C.). In a preferred version of the invention, the hydroxylated aromatic compounds are phenol and its derivatives, and the aromatic compounds are benzene and its derivatives.

Applicants do not wish to be bound by any particular theory of operation of the invention. However, Applicants offer the following explanation of how the temperature treatment affects the catalyst. The purpose of the two-step high-temperature treatment is related to the generation of a specific type of Lewis acid-base pair centers, preferably framework Lewis acid-base sites. This is achieved by separating the stage of removal of adsorbed water and/or ammonium ions (which are introduced via ion exchange at the stage of the preparation of an H— or $NH_4$-forms of zeolites), from the stage of removing structural (bridging) OH groups intrinsic to the H-zeolite framework. For this purpose, the thermal treatment is carried out in two steps. In the first step, the zeolite is calcined at a temperature up to 350–450° C. (a conventional pretreatment). In this first step, adsorbed water and exchanged ammonium ions are intensively removed. In the second step, the zeolite is calcined at temperatures ranging from 450 to 950° C., depending on the zeolite composition. In this second step, structural (acidic) OH groups of zeolites are removed. This second step can solve two problems: (1) removing acidic OH groups that are the active sites for side reactions leading to the formation of tar-like products; and (2) creating new (aprotic) rather strong Lewis acid-base pairs, preferably related to the framework of the zeolite, that are capable of activating $N_2O$ molecules to cause evolution of molecular nitrogen and formation of atomic oxygen species adsorbed on strong Lewis acid sites. The atomic oxygen acts as a mild oxidizing agent in the reaction of selective oxidation of aromatic compounds to corresponding hydroxylated aromatic compounds. The strong Lewis acid-base centers as precursors of the active oxidizing centers (atomic oxygen) can be detected by IR spectroscopy using adsorbed probe-molecules, such as CO, $H_2$, $CH_4$, etc.

DETAILED DESCRIPTION OF THE PREFERRED EMBODIMENTS OF THE INVENTION

According to the present invention, the starting materials for the preparation of the zeolite catalysts are the commercial forms of zeolites, such as:

(1) high-silica pentasil-type zeolites like ZSM-5, ZSM-11 etc., prepared, for instance, as described in U.S. Pat. No. 3,702,886, which is hereby incorporated by reference;

(2) zeolite H-mordenite; or (3) isomorphously substituted pentasils like ferrisilicate, gallosilicate etc.

Preferably, a commercial ZSM type zeolite (ZSMe-5, ZSM-11, ZSM-12, ZSM-23 etc.) with Si/Al or Si/Me ratios (where Me=Ga, Fe) greater than 20 is used in the present invention. In more preferred versions of the invention, the Si/Al or Si/Me ratio ranges from 40 to 100.

According to the present invention, the commercial zeolite is acidified by addition thereto of an inorganic or organic acid. In a preferred embodiment of the invention, the zeolite is acidified by soaking it with from 10 ml to 100 ml of acid per gram of a zeolite, wherein the acid has a normality of from 0.1 N to 2 N. The acid soaking may be done in a single step, or more preferably, in several steps.

Acid forms of zeolite may be also prepared by exchanging of a commercial zeolite with an aqueous solution of an ammonium salt (e.g., a nitrate or chloride salt). For example, a Na-form of ZSM-type zeolite is treated with a 0.1–2 N solution of an appropriate ammonium salt The ion exchange degree of sodium for ammonium or protons is varied from 30 to 100%, and more preferably from 50 to 95%.

Zeolites can be used as catalysts in the pure form or in a combination with an appropriate binder. In a preferred embodiment of the invention, amorphous silica with a specific surface area ranging from 100 to 600 $m^2/g$, or alumina with a specific surface area ranging from 100 to 400 $m^2/g$, or a mixture thereof, are used as binders. The content of the binder in the catalyst ranged from 5 to 50 wt %, and more preferably from 20 to 30 wt %.

Nitrous oxide may be employed alone, or in admixture with an inert gas such as nitrogen or helium, or in admixture with air.

Aromatic hydrocarbons, such as benzene, toluene, ethylbenzene, cumene, xylenes and the like, the halogenated aromatic compounds such as chlorobenzene, fluorobenzene, difluorobenzenes and the like, phenol, styrene or a mixture thereof are typically used as substrates for selective oxidation with nitrous oxide. It is also possible to selectively further oxidize an aromatic compound such as phenol, using the process described herein. For purposes of this specification, these substrate materials will be generally referred to as "aromatic compounds."

In the process described herein, the substrate is typically introduced in a mixture with nitrous oxide in a molar ratio of nitrous oxide to substrate ranging from 1:7 to 5:1, and more preferably, from 1:2 to 4:1. The LHSV of the substrate ranged from 0.2 to 5 $h^{-1}$, more preferably from 0.5 to 2 $h^{-1}$. The reaction is preferably carried out at a temperature from 300 to 500° C., and more preferably from 350 to 450° C. The contact time of the reaction mixture with a catalyst ranges from 0.5 to 8 sec, and more preferably from 1 to 4 s.

The gases evolved from the reactor may comprise a mixture of phenol and dihydroxybenzenes and are condensed and separated by any technique known to this art (GC, LC, MS or a combination thereof).

The catalyst can be easily and reversibly regenerated by calcination at 400–600° C. in a flow of air, oxygen, and nitrous oxide, or mixtures thereof with an inert gas. The regeneration is carried out for 1–3 h.

In order to further illustrate the present invention and the advantages thereof, the following specific examples are given, it being understood that same are intended only as illustrative and in no way limitative.

In said examples below, the following parameters, are used: C=percentage of conversion, S=percentage selectivity, Y=yield based on the product passed=C×S. The characteristics reported in the Examples are averaged over a two hour time period on stream.

EXAMPLE 1

Synthesis of the starting HZSM-5 zeolite was carried out as described in U.S. Pat. No. 3,702,886, which is hereby incorporated by reference.

Experimental conditions of benzene oxidation with nitrous oxide:

| | |
|---|---|
| Vapor phase | continuous |
| Catalyst | HZSM-5 ($SiO_2/Al_2O_3$ = 42) |
| Standard pretreatment temperature | 350° C. |
| High-temperature calcination at | 450, 650, 750, 850, 920 or 1100° C. |
| Reaction temperature | 350° C. |
| Molar ratio | Benzene/$N_2$/$N_2O$ = 2/5/8 |

200 mg of catalyst HZSM-5 (Si/Al=21) in powder form (particle size of 0.2–0.5 mm) dispersed in 400 mg of quartz grains of the same size were placed into a tubular reactor constructed of quartz or stainless steel (with an internal diameter of 7 mm). Prior to the reaction, the catalyst was pretreated in two stages. The first stage was a conditioning of the catalyst for 5 h at 350° C. under nitrogen or air flow (60 ml/min) in a tubular oven. The second stage was a mild high-temperature calcination step comprising heating the catalyst for an additional two hours at a higher temperature (450,650, 750,850,920 or 1100° C.) in a continuous nitrogen or air flow. After this treatment, the catalyst was cooled down to the reaction temperature (i.e., 350° C.) in flowing nitrogen. The reaction was carried out continuously by introducing a mixture of: benzene with a LHSV of 0.5–2 $h^{-1}$, nitrous oxide and helium (nitrogen). The mixture's contact time was 1–4 sec.

The data on the conversion, selectivity and yield of phenol versus the final temperature of the high-temperature pretreatment, are presented in Table 1. Also, the percent of deactivation (i.e., a decrease of the conversion during the following 60 min of time on stream) is given in Table 1. As seen from this table, the high-temperature treatment in dry air leading to the formation of the framework coupled Lewis acid-base centers considerably enhances the catalytic activity. At a temperature above 1000–1100° C., a collapse of the structure of the HZSM-5 zeolite takes place, thereby resulting in a drop of the activity.

TABLE 1

Benzene oxidation at 350° C. on HZSM-5 zeolite (Example 1)

| Conditions of high-temperature treatment, ° C. | C, % | S, % | Y, % | Deactivation (during 60 min), % |
|---|---|---|---|---|
| 350 | 10 | 97 | 9.7 | 50 |
| 450 | 12 | 95 | 11.4 | 42 |
| 650 | 16 | 95 | 15.2 | 45 |
| 750 | 21 | 96 | 20.2 | 42 |
| 850 | 29 | 94 | 27.8 | 14 |
| 920 | 36 | 98 | 35.3 | 11 |
| 1100 | 0 | — | — | — |

EXAMPLE 2

The catalyst preparation and catalytic testing were done as described in Example 1, with the exception that a higher reaction temperature of 450° C. was employed. The data obtained are shown in Table 2.

These data show that if a higher reaction temperature (e.g., about 450° C.) is employed, the activity, and especially the selectivity, of the catalyst increases with increasing temperature of the high-temperature calcination. Thus, for the catalyst developed in the present invention, the reaction of direct oxidation of benzene into phenol proceeds with a selectivity close to 100% even at high reaction temperatures.

TABLE 2

Benzene oxidation at 450° C. on HZSM-5 zeolite (Example 2)

| Conditions of high-temperature treatment, ° C. | C, % | S, % | Y, % | Deactivation (during 60 min), % |
|---|---|---|---|---|
| 350 | 47 | 38 | 17.8 | 24 |
| 450 | 51 | 35 | 17.9 | 18.5 |
| 650 | 55 | 37 | 20.4 | 18 |
| 750 | 52 | 41 | 21.3 | 17 |
| 850 | 54 | 68 | 36.7 | 15 |
| 920 | 58 | 95 | 55.1 | 11 |
| 1100 | 0 | — | 0 | — |

EXAMPLES 3 AND 4

The catalyst preparation and catalytic testing were done as in Examples 1 and 2, respectively, except for the type of the catalyst used. In order to determine the dependence of the catalytic parameters on the Si/Al ratio in the framework, HZSM-5 zeolite with Si/Al=50 (Example 3) and HZSM-5 with Si/Al=21 (Example 4) were compared. In these tests, the benzene partial pressure was 60–80 torr. The results of the evaluation are summarized in Table 3. The increase in the Si/Al ratio in the zeolite results in a 100% selectivity to phenol. This 100% selectivity is maintained over a wide range of preliminary high-temperature treatments.

TABLE 3

Comparison of the catalytic properties of zeolites with different Si/Al ratio in benzene oxidation

| Conditions of high temperature treatment, ° C. | Si/Al = 50 (Example 3) | | | Si/Al = 21 (Example 4) | | |
|---|---|---|---|---|---|---|
| | C, % | S, % | Y, % | C, % | S, % | Y, % |
| Reaction temperature 350° C. | | | | | | |
| 550 | 2 | 100 | 2 | 14 | 95 | 13.3 |
| 650 | 13 | 100 | 13 | 16 | 95 | 15.2 |
| 750 | 21 | 100 | 21 | 21 | 96 | 20.2 |
| Reaction temperature 450° C. | | | | | | |
| 450 | 70 | 85 | 59.5 | 51 | 35 | 17.9 |
| 750 | 77 | 90 | 69.3 | 52 | 41 | 21.3 |
| 850 | 75 | 100 | 75 | 54 | 68 | 36.7 |

EXAMPLES 5

The zeolite HZSM-5 (Si/Al=21) prepared via acid treatment or $NH_4$-in Example 1, was calcined at 450° C. for 5 h (Cycle 1), then at 800° C. for 2 h in flowing air. After this treatment, the catalyst was cooled down to room temperature, and was kept in contact with water vapor during 24 h (Cycle 2) next, the sample was again calcined at 450, 650 or 800° C. for 2 h, and the reaction of benzene oxidation with $N_2O$ was carried out at 350° C. as described in Example 1. The results of catalytic experiments are presented in Table 4.

These data show that the catalyst, after pretreatment under conditions of high-temperature calcination exhibits better activity than the fresh catalyst treated under standard conditions (~450° C.). This holds true even if the pretreated catalyst is subsequently hydrated and calcined a second time at 450–500° C. Thus, once the coupled framework Lewis acid-base centers are formed, they survive saturation with water vapor provided that further calcination is performed at temperatures above 450° C.

TABLE 4

Influence of the pretreatment conditions on the activity and selectivity in direct benzene oxidation (Example 5)

| Pretreatment conditions | C, % | S, % |
| --- | --- | --- |
| 1. Activation at 450° C. (Cycle 1) | 12 | 95 |
| 2. Cycle 1 + activation at 800° C. + Cycle 2 + activation at 450° C. | 24 | 96 |
| 3. Cycle 1 + activation at 800° C. + Cycle 2 + activation at 650° C. | 30 | 95 |
| 4. Cycle 1 + activation at 800° C. + Cycle 2 + activation at 800° C. | 34 | 97 |
| 5. Activation at 650° C. | 16 | 95 |

EXAMPLE 6

2.3 g of the catalyst prepared according to Example 3, and pretreated at 900° C., was loaded (particle size, 1–2 mm). Benzene was supplied with a space velocity of 0.5 h$^{-1}$, and the $N_2O:C_6H_6$ ratio is 2:1. The benzene partial pressure was 120 torr (the benzene content in the vapor phase was 16 mol. %). At the reaction temperature 370° C., the yield of phenol was 25%, and the selectivity was 100%. At the reaction temperature of 420° C., the yield was 32%, the selectivity was 99%.

EXAMPLE 7

2.3 g of the catalyst prepared according to Example 3, and pretreated at 900° C., was loaded in the reactor (particle size, 1–2 mm). Benzene was supplied with a LHSV of 0.3 h$^{-1}$ and the $N_2O:C_6H_6$ ratio was 1:1. At a 370° C. reaction temperature, the yield of phenol was 37% and the selectivity was 100%. At 420° C., the yield was 49%, and the selectivity was 99%. The efficiency of $N_2O$ utilization for selective oxidation of benzene to phenol was 98%.

EXAMPLE 8

2.3 g of the HZSM-5 zeolite (particle size, 1–2 mm) with Si/Al=40 was prepared according to Example 3, pretreated at 850° C., and was loaded in the reactor. Benzene was supplied with a LHSV of 0.5 h$^{-1}$ and the $N_2O:C_6H_6$ ratio was 0.5:1. At a 400° C. reaction temperature, the yield of phenol based on $N_2O$ was 28.3%, and the selectivity was 99%. Alternatively, the yield on the basis of benzene was 14.2%. At 420° C., the phenol yield on the basis of $N_2O$ was 33.6%, and the selectivity was 98%. Alternatively, the yield on the basis of benzene was 16.8%. The efficiency of $N_2O$ utilization for selective oxidation of benzene to phenol was 96%.

EXAMPLE 9

2.3 g of the HZSM-5 zeolite (particle size, 1–2 mm) with Si/Al=40 was prepared according to Example 3, pretreated at 850° C., and was loaded in the reactor. Benzene was supplied with a LHSV of 0.3 h$^{-1}$, and the $N_2O:C_6H_6$ ratio was 0.5:1. At a 420° C. reaction temperature, the yield of phenol based on $N_2O$ was 28.2%, and the selectivity was 98%. The efficiency of $N_2O$ utilization for selective oxidation of benzene to phenol was 95%.

EXAMPLE 10

2.3 g of the HZSM-5 zeolite (particle size, 1–2 mm) with Si/Al=40 was prepared according to Example 3, pretreated at 850° C., and loaded in the reactor. Benzene was supplied with a LHSV of 0.5 h$^{-1}$, and the $N_2O:C_6H_6$, ratio was 1:1. A mixture of $N_2O$ and air (1:3) was used as an oxidant. At 370° C., the yield of phenol was 26.8%, and the selectivity was 98%.

EXAMPLE 11

The HZSM-5 zeolite (Si/Al=40) was extruded with a SiO2 binder (20% $SiO_2$+80% HZSM-5) and the extrudates (cylinders 2×2 mm) were calcined in two steps according to the procedure described in Example 1. The final temperature of the high temperature treatment was 900° C. The catalyst was tested in benzene oxidation with $N_2O$. In this test, the benzene LHSV was 1.7 h$^{-1}$, the benzene-to-$N_2O$ molar ratio was 7:1 (a large excess of benzene over $N_2O$), and the temperature was 440–470° C. The yield of phenol (on the basis of $N_2O$) was 20.6% at 440° C. and 30.2% at 470° C. The efficiency of $N_2O$ utilization for selective oxidation of benzene to phenol was 95–96%.

EXAMPLE 12

A gallium-modified HEM-5 zeolite was prepared by impregnation of a HZSM-5 zeolite with an aqueous solution of gallium nitrate, followed by calcination at 500° C. for 4 h to remove the nitrate ions (the Ga2O3 content was 3 wt %). The zeolite was subsequently pretreated at 850° C. and was loaded in the reactor. 2.3 g (particle size, 1–2 mm) of the zeolite was treated in this manner. Benzene was supplied with a LHSV of 0.5 h$^{-1}$ at the $N_2O:C_6H_6$ ratio of 0.5:1. At the 420° C. reaction temperature, the yield of phenol was 20.8% on the basis of $N_{22}O$, or 10.4% on the basis of benzene. The selectivity was 100%. The efficiency of $N_2O$ utilization for selective oxidation of benzene to phenol was 100%.

EXAMPLES 13 AND 14

250 mg of 0.5–1.0 mm particle size catalyst was prepared according to Example 3. This catalyst was diluted with quartz grains (750 mg), and the mixture was loaded into the reactor. Benzene (Example 13) and phenol (Example 14) were used as substrates. The nitrous oxide: substrate ratio was 4:1, the LHSV was 0.5 h$^{-1}$, and the reaction temperature 430° C. In the case of benzene, a product comprising 75% phenol and 25% of a mixture of o- and p-diphenols (in a 1:4 ratio) was obtained. The overall yield was 60%, and the selectivity was 97%. In the case of phenol, a mixture of o-, m-, and p-diphenols in the ratio 1.0: 0.5:4.0 with the overall yield of 75% was produced.

EXAMPLES 15–20

500 mg of the catalyst prepared according to Examples 1 and 2 was placed in a flow setup. The substrates used were fluorobenzene, o-, m-, p-difluorobenzene, toluene, p-xylene, ethylbenzene, and styrene (Examples 15–20, respectively). The ratio in the gas mixture was He: air: nitrous oxide=

1:3:5. The LSHV of the substrate was 1–3 h$^{-1}$. The N$_2$O: substrate ratio was 4:1. The data on the oxidation of the substrates are given in Tables 5–7. Several values for the conversion in the tables correspond to different reaction times of 10, 40, and 70 min. It was observed that the conversion of alkylbenzenes (Table 7) decreases with time. This observation can be explained by catalyst deactivation. In the case of fluorobenzene oxidation, a mixture containing predominantly p-fluorophenol (up to 75% in the mixture) is produced without formation of the m-isomer.

TABLE 5

Oxidation of fluorobenzene on the zeolite catalyst (Example 15)

| Liquid Space velocity, h$^{-1}$ | T, ° C. | C, % | Selectivity to fluorophenol % |
|---|---|---|---|
| 2.3 | 400 | 52 | 92 |
|  |  | 25 |  |
| 1.0 | 400 | 60 | 92 |
|  |  | 39 |  |
|  |  | 27 |  |
| 1.0 | 450 | 74 | 60 |
|  |  | 58 |  |
|  |  | 56 |  |

TABLE 6

Oxidation of difluorobenzenes on the zeolite catalyst (Example 16)

| Substrate | T,° C. | C, % | Selectivity to dilurophenol % | Selectivity to fluorophenol, % |
|---|---|---|---|---|
| o-difluorobenzene | 400 | 30 | 84 | 16 |
| m-difluorobenzene | 400 | 23 | 82 | 18 |
| p-difluorobenzene | 450 | 44 | — | — |

TABLE 7

Oxidation of alkylbenzenes on the zeolite catalyst

| Examples | T, ° C. | Alkylbenzene | C, % | Yield of alkylphenol, % | Other Products (yield, %) |
|---|---|---|---|---|---|
| 16 | 350 | p-xylene | 22 | 8 | toluene pseudocumene (40) |
|  | 400 |  | 44 | 16 | toluene, pseudocumene (25) |
| 17 | 400 | toluene | 25 | 22 | — |
| 18 | 400 | ethylbenzene | 60 | 20 | styrene (34) |
|  | 450 |  | 85 | 20 | styrene (37), benzofuran (14) |
| 19 | 350 | styrene | 10 | 0 | benzofuran (5) |
|  | 400 |  | 37 | 0 | benzofuran (10) phenylacetic aldehyde, acid (13) |

EXAMPLE 21

HZSM-5 zeolite containing Ga$^{3+}$ ions in the framework, which were introduced during the synthesis (Si/Ga=40), was subject to high-temperature treatment by stepwise calcination at 450° C. for 5 h and at 750° C. for 2 h. Fluorobenzene oxidation was carried out using this catalyst wherein LHSV of benzen is 2.3 h$^{-1}$, reaction temperature is 400° C., and the composition of the gas mixture is air: N$_2$O: He=3:5:2. The N$_2$O: substrate ratio was 1:4. Under these conditions, the fluorophenol yield was 20%, and the selectivity was 97%. The para-isomer predominates among the fluorophenols produced (70%).

To summarize, the examples show that the presently invented catalysts, where applied to oxidize benzene and its derivatives into corresponding phenols in the presence of nitrous oxide as an oxidant, exhibit the following advantages over the known catalysts reported in the patents:

(1) The benzene conversion for the catalysts according to the invention may be increased from 10–20% to 50–75% without decreasing the selectivity (~98–100%);

(2) The selectivity of phenol production at a high reaction temperature (~400–470° C.) may be increased from 30–40% to 95–100%, and the phenol yield may be increased up to 70%;

(3) The efficiency of N$_2$O utilization for the selective oxidation of the aromatic compounds can be increased from 80–85% to 95–100%;

(4) When a zeolite catalyst which has been subjected to the preliminary high-temperature pretreatment is used, the use of a higher partial pressures of benzene, and lower N$_2$O: benzene ratios may be employed. This produces a decrease in the consumption of nitrous oxide, and an increase in the phenol productivity;

(5) The stability and the life time of a catalyst may be considerably improved by modifying a zeolite catalysts to introduce strong Lewis acid-base sites. These sites have a specific nature, and are created by high-temperature calcination of the zeolites preceding the catalytic testing;

(6) The high yield and selectivity of phenol formation can be achieved without introduction of special iron additives into the catalyst and steam treatment;

(7) In some cases of oxidation of benzene derivatives (e.g., halogenated benzenes, phenols), the process has high selectivity and regioselectivity toward p-isomers of the phenols.

While the invention has been described in terms of various preferred embodiments, the skilled artisan will appreciate that various modifications, substitutions, omissions and other changes may be made without departing from the spirit thereof. Accordingly, it is intended that the scope of the present invention shall not be limited to the preferred embodiments of the invention described herein.

We claim:

1. A process for preparing a hydroxylated aromatic compound by oxidation of a monocyclic aromatic compound, wherein said hydroxylated aromatic compound has one more hydroxyl group than said aromatic compound, which process comprises: combining said aromatic compound with nitrous oxide at a reaction temperature between 225–500° C., and exposing said nitrous oxide and said aromatic compound to a heterogeneous catalyst composition comprising a high silica pentasil-type zeolite wherein said zeolite has been pretreated according to an activation procedure comprising:

(a) first, heating the H-form of the zeolite at a first temperature in the range of 350–450° C. in a first flowing gas for 4–6 h;

(b) second, calcining the zeolite at a second temperature in the range of 450–1000° C. for 1–3 h in a continuous flow of a second gas, wherein said second temperature is at least 100° C. greater than said first temperature; and (c) third, cooling the zeolite catalyst to the reaction temperature, thereby forming the heterogeneous catalyst composition.

2. A process according to claim 1, wherein said hydroxylated aromatic compound is selected from the group consisting of phenol, diphenols, chorophenols, fluorophenols, difluorophenols, and alkyl phenols.

3. A process according to claim 2, wherein said aromatic compound is selected from the group consisting of benzene, phenol, fluorobenzene, chlorobenzene, 1, 2difluorobenzene, 1, 3-difluorobenzene, 1, 4-difluorobenzene, styrene, and mono, di and trialkylbenzenes having alkyl groups comprising 1 to 3 carbon atoms.

4. A process according to claim 3, wherein the first flowing gas is selected from the group consisting of nitrogen and air, and the second of gas is selected from the group consisting of an inert gas and air.

5. A process according to claim 1, wherein the high-silica pentasil zeolite is an H-form of ZSM-5 zeolite, wherein the Si/Al ratio ranges from 20 to 100.

6. A process according to claim 5, wherein the Si/Al ratio ranges from 30 to 50.

7. A process according to claim 1, wherein the reaction temperature is from 300 to 500° C.

8. A process according to claim 1, wherein the molar ratio of $N_2O$: aromatic compound ranges from 1:7 to 10:1.

9. A process according to claim 1, wherein the molar $N_2O$: aromatic compound ratio is in the range of from 0.5:1 to 1:1.

10. A process according to claim 1, wherein an inert gas diluent is added to the aromatic compound and nitrous oxide combination, wherein the diluent is selected from the group consisting of $N_2$, He, and Ar.

11. A process according to claim 1, wherein a diluent is added to the aromatic compound and nitrous oxide combination, wherein said diluent is selected from the group consisting of air and mixtures of air with inert gases.

12. A process according to claim 1, wherein a diluent is added to the aromatic compound and nitrous oxide combination, wherein said diluent is selected from the group consisting of oxygen and mixtures of oxygen with inert gas(es).

13. A process according to claim 1, wherein the zeolite comprises gallium, and the silica to gallium ratio is from 10 to 100.

14. A process according to claim 13, wherein the zeolite is an isomorphously substituted gallosilicate pentasil zeolite.

15. A process according to claim 13, wherein prior to the activation procedure the zeolite is impregnated with a gallium salt, and subsequently calcined in air.

16. A process according to claim 15, wherein said calcining step is performed at a temperature ranging from 550 to 800° C.

17. A process as claimed in claim 1, wherein the heterogeneous catalyst composition further comprises a binder, wherein the weight content of the binder ranges from 1.0 to 99.0 wt %.

18. A process according to claim 17, wherein the weight content of the binder ranges from 10 to 30 wt %.

19. A process according to claim 17, wherein the binder is selected from the group consisting of silica, alumina, and mixtures thereof.

20. An improved process for oxidizing an aromatic compound, which process comprises: reacting said aromatic compound with nitrous oxide at a reaction temperature of 225–500° C., wherein the improvement comprises contacting the aromatic compound with nitrous oxide in the presence of a heterogeneous catalyst composition comprising a high-silica pentasil-type zeolite wherein said zeolite has been pretreated according to an activation procedure comprising: (a) first, heating the H-form zeolite at a first temperature in the range of 350–450° C. in a first flowing gas for 4–6 h; (b) second, calcining the zeolite at a second temperature in the range of 450–1000° C. for 1 –3 h in a continuous flow of gas, wherein said second temperature is at least 100° C. greater than said first temperature; and (c) third, cooling the zeolite to the reaction temperature, thereby forming the heterogeneous catalyst composition.

* * * * *